US008083065B2

(12) United States Patent
Musse

(10) Patent No.: US 8,083,065 B2
(45) Date of Patent: Dec. 27, 2011

(54) NURSING TRAY

(76) Inventor: Madina Musse, Roslindale, MA (US)

(*) Notice: Subject to any disclaimer, the term of this patent is extended or adjusted under 35 U.S.C. 154(b) by 0 days.

(21) Appl. No.: 12/411,126

(22) Filed: Mar. 25, 2009

(65) Prior Publication Data
US 2009/0242454 A1 Oct. 1, 2009

Related U.S. Application Data

(60) Provisional application No. 61/039,289, filed on Mar. 25, 2008.

(51) Int. Cl.
B65D 1/36 (2006.01)

(52) U.S. Cl. .......... 206/564; 206/570; 206/365

(58) Field of Classification Search .......... 206/570, 206/365, 557–567; 108/132, 129
See application file for complete search history.

(56) References Cited

U.S. PATENT DOCUMENTS

| 1,885,483 | A | * | 11/1932 | Samuelson | 206/553 |
| D146,697 | S | * | 4/1947 | Bates | D7/553.8 |
| 4,083,453 | A | * | 4/1978 | Berger et al. | 206/565 |
| 5,353,952 | A | * | 10/1994 | Donche | 220/575 |
| 5,383,411 | A | * | 1/1995 | Tomaka et al. | 108/129 |
| 5,390,798 | A | * | 2/1995 | Yanuzzi | 206/562 |
| 6,474,472 | B1 | * | 11/2002 | Shaw | 206/366 |
| 6,517,002 | B1 | | 2/2003 | Piatek | |
| 7,097,099 | B2 | | 8/2006 | Hepworth et al. | |
| 7,137,752 | B2 | * | 11/2006 | Hendee | 402/73 |
| D576,455 | S | * | 9/2008 | Siddle | D7/701 |

* cited by examiner

Primary Examiner — J. Gregory Pickett
Assistant Examiner — Andrew Perreault
(74) Attorney, Agent, or Firm — Hiscock & Barclay, LLP

(57) ABSTRACT

A tray for organizing various objects, e.g., medications, their receptacles and medical implements, that are needed in a typical nursing task is provided. The tray is advantageously constructed to balance all the objects during transport and during use such that its contents are prevented from toppling over in motion or in station.

19 Claims, 4 Drawing Sheets

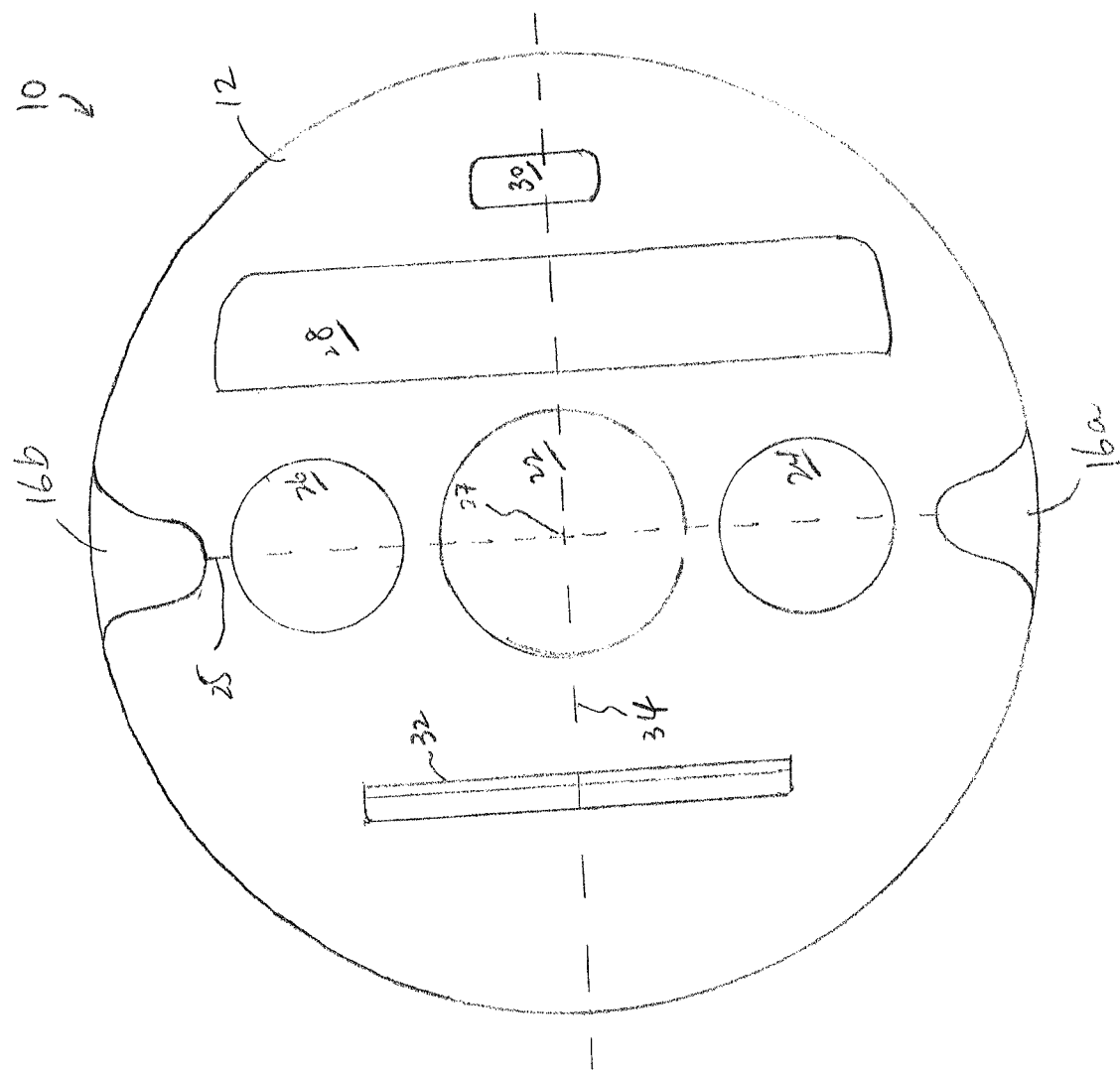

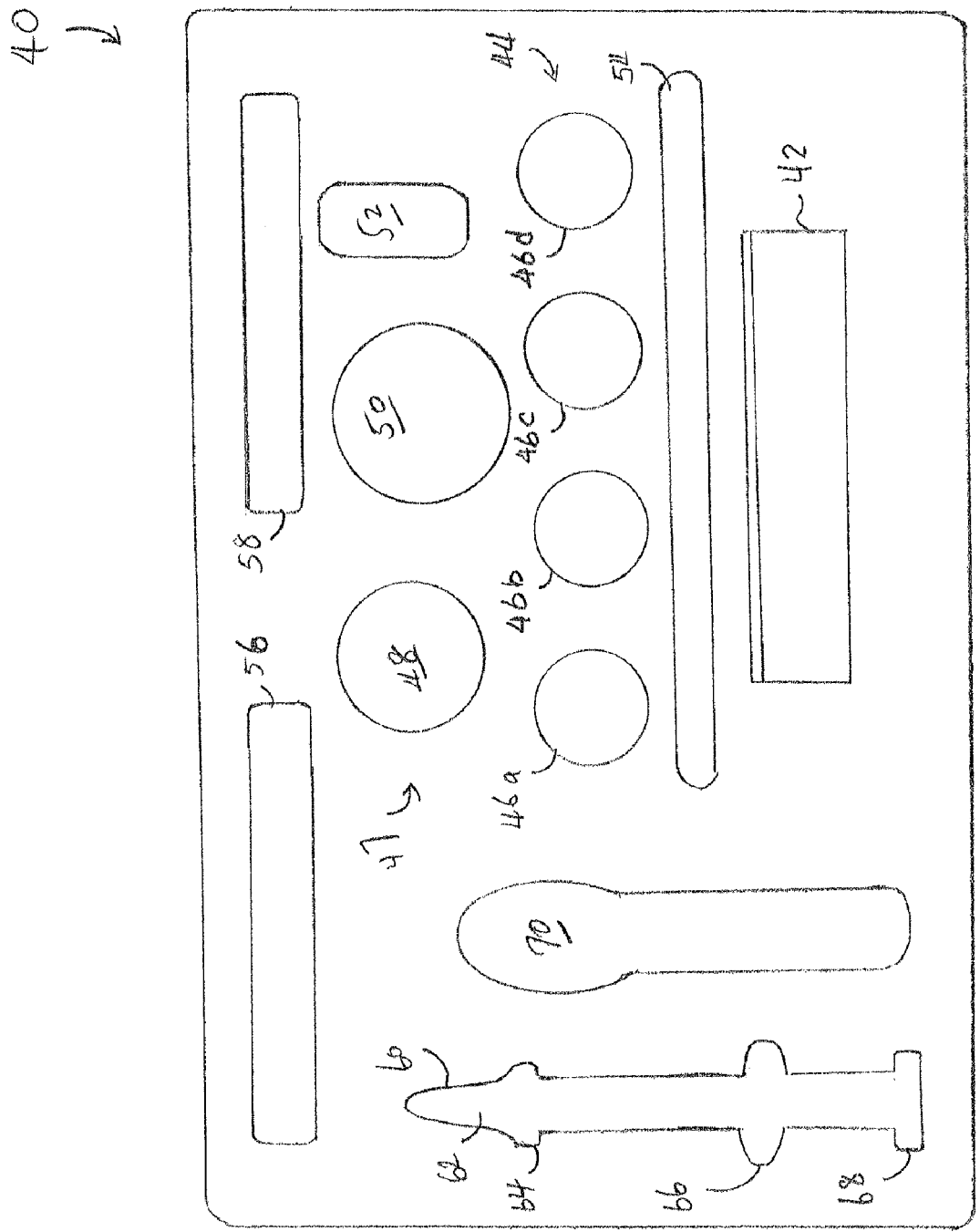

NURSING TRAY

CROSS-REFERENCE TO RELATED APPLICATIONS

This application claims priority to and the benefit of U.S. provisional patent application Ser. No. 61/039,289, filed Mar. 25, 2008, which application is incorporated herein by reference in its entirety.

BACKGROUND OF THE INVENTION

The present invention relates generally to holders and organizers for items used in the medical and nursing profession. More particularly, the present invention relates to a tray with recesses and depressions defined thereupon for organizing and transporting multiple objects needed for treating, nursing or tending to a patient.

An important factor in a patient's successful convalesce is the nursing process during which prescribed medications should be administered to the patient on time while the patient is consoled and comforted. Most of the time, these tasks fall on the shoulders of the nurses, nurse assistants, attendants and other healthcare staff. However, many healthcare facilities are severely short-handed in nursing staff. While struggling with increasingly complex medication regimens, nurses are often interrupted during their tasks as they answer doctors, family members, pages and telephone calls. If a nurse is on her way toward a patient with a tray full of medications, and she is stopped by a doctor telling her about special treatment needed for another patient, without access to a notepad and a writing instrument, she has to memorize the new information regarding the second patient. In doing so, she might forget what she needs to do with regard to the original patient or even his name, and has to go back to her station to look up that information again. Obviously, this kind of interruptions can give rise to severe consequences when the wrong dosage or medication is administered-with many medications being so potent nowadays, nurses need every bit of help in battling human mistakes, for example, when administering narcotics. Also patients are often in a state where their faculties are compromised to some extent, and with the high turnover rate of both patients and nursing staff, nurses constantly have to check patient identification, often without much help from the patient himself.

Therefore, there is a need, unfulfilled by the current products in the market, for a device or apparatus that helps nursing personnel organize multiple objects needed for tending to a patient that also allows them to go back to what they were doing before they were interrupted and to continue with that original task without making mistakes.

Prior art applications have often focused on organizing medications automatically or according to the time intervals prescribed for taking the medication. Some of them resort to computers and microprocessors. Accordingly, one of the objectives of the present invention is to provide a simple apparatus that helps the nursing personnel in their organization and effort to minimize the chances of making mistakes while remaining inexpensive to manufacture. A further objective is to provide an apparatus that helps with the transport of multiple objects, including multiple fluids, that are needed for tending patients. Another objective is to provide in a nursing tray prefabricated spaces designed to hold medical instruments and containers of various sizes.

BRIEF SUMMARY OF THE INVENTION

The present invention provides a tray or a similar device for organizing and transporting multiple medications and other objects needed for tending a patient. The tray of the present invention includes a display area. The display may show identity information regarding the patient—this not only reminds the nurse for whom the medication is intended but also gives visual reassurance to a patient when he sees his own name thereon. The tray also may include spaces and structures for depositing a writing instrument and a notepad. The present invention helps a nursing personnel stay organized, reduce mistakes, and spend more time caring for the patient.

In one aspect, the tray of the present invention is easy to balance while one is transporting the tray. It is also less likely to topple over while being set down on a level surface. In particular, a tray for transporting and serving medication is provided with a substantially planar body having a top surface and a bottom surface, the body further has a perimetrical surface connecting at least part of the top surface and part of the bottom surface and defining a general thickness of the tray. The tray has first and a second grasping features substantially opposite each other on the side. The two grasping features (e.g., thumb depressions) together define a grasping line across the top surface. The tray also includes a plurality of depressions situated on the top surface and substantially in the grasping line forming a row, each depression sized and shaped for receiving a receptacle. The depressions are sized and shaped for receiving various types of receptacles, some of substantially round cross-sections, some of substantially oval cross-sections.

In one feature, the tray also has at least one elongated depression with its long axis running substantially parallel to the grasping line. The elongated depression, in one embodiment, is sized and shaped for receiving a syringe. In particular, the depression may include at least two notches for receiving the syringe in an extended or collapsed state.

In another feature, the tray may include a display and a structure for fastening a writing instrument thereonto.

In yet another feature, an orthogonal line runs through a midpoint of the grasping line dividing the body into two substantially even halves, and all the depressions and the display are situated symmetrical about the orthogonal line. In one embodiment, all the depressions and the display are arranged in rows that run substantially parallel to the grasp line defined by two grasping features. These features help the user balance various objects on the tray during transportation.

BRIEF DESCRIPTION OF THE DRAWINGS

FIG. 2 is a top view of the embodiment shown in FIG. 1.

FIG. 4 is a perspective view of another embodiment of the invention.

DETAILED DESCRIPTION OF THE INVENTION

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the course of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In general, the present invention provides a tray, caddy, holder or similar apparatus that supplies prefabricated space for one or more of the following:

I. Recesses and depressions for cups and containers for medications and liquids with which to take the medications;

II. Display surface for displaying patient identification and other medical information;

III. Slot or depression for notes, a notepad, or Post-it® notes;

IV. Structure for holding a writing instrument;

V. Recess or depression for common external medications such as a bottle of nasal spray, eye drops, ear drops, skin medications, lotions, and/or antiseptics;

VI. Slot or depression for a syringe; and

VII. Slot or depression for other instruments commonly used in nursing such as spoon, straw and thermometer.

The items listed above have been found to be most useful for a busy nursing staff member taking care of patients. However, the invention also contemplates other items commonly needed for performing a nursing task, and making prefabricated space for those item in the tray is within the claimed coverage. Now we turn to some preferred embodiments to illustrate the principles behind the present invention.

Figure 1:
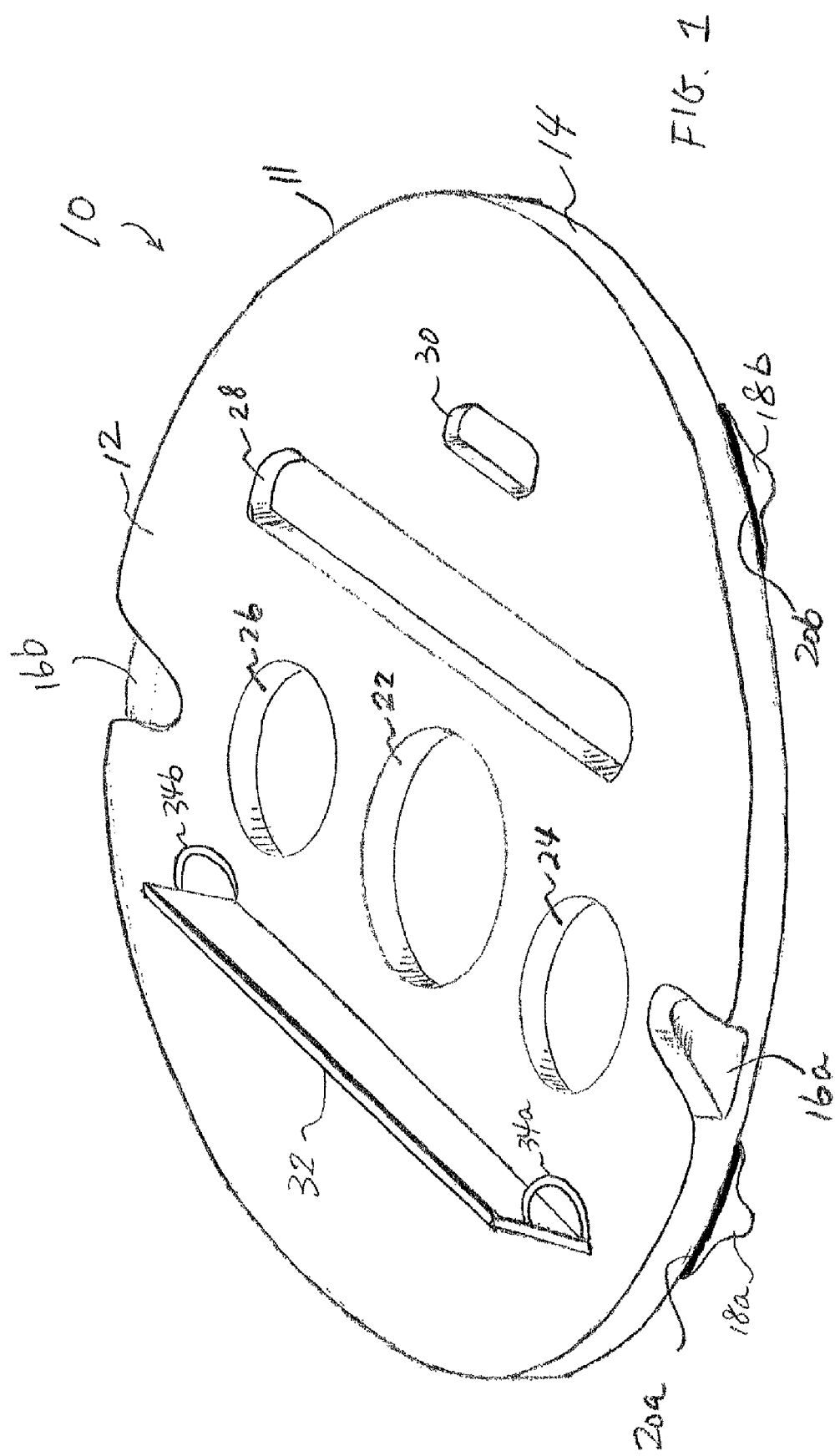
FIG. 1 is a perspective view of an embodiment of the invention.
Figure 3C:
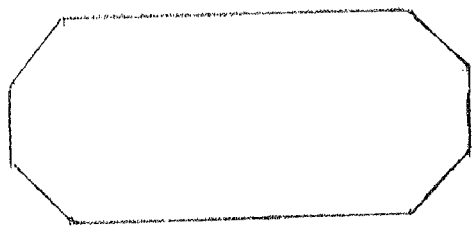
FIGS. 3A-3D are various examples of a "substantially oval" shape described with regard to some of the depressions in embodiments of the invention.
Figure 3B:
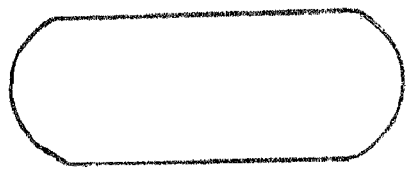
Figure 3D:
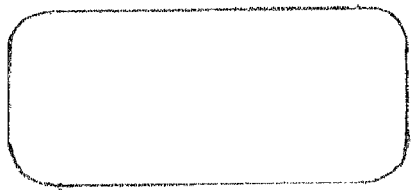
Figure 3A:
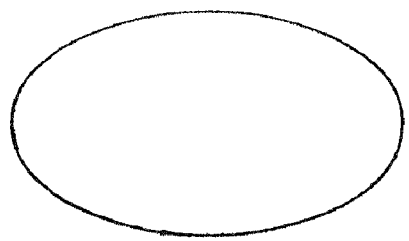

Referring now to FIGS. 1 and 2, a tray for transporting and serving medication according to the present invention is shown, generally indicated by 10. The tray 10 has a substantially planar body 11 that has a top surface 12 opposite a bottom surface (not shown); the two surfaces are connected by a perimetrical or side surface 14. The tray can be of any shape, round, oval, rectangular, square or irregular. Tray 10 as illustrated here happens to be substantially round. In one feature, the tray is dimensioned to fit into a drawer of a medication cart. For example, a drawer for one popular mediation cart is about 18 inches by about 10 inches in dimension, and the tray embodiments of the present invention can be dimensioned to be less than that size. In one embodiment, the tray 10 is about 9 inches or 8 inches in width or diameter. The bottom surface is substantially planar and should match the top surface 12 substantially in size and shape, although it can be easily envisioned to be slightly larger or smaller, either for ease of construction, grasping or other purposes. The perimetrical surface 14 defines the thickness of the tray 10 and, in one embodiment, is between about 0.25 inch and about 1.0 inch. Two thumb depressions 16a and 16b are situated across from each other along the outer edge of the top surface 12. Each of the thumb depressions 16a and 16b is shaped and sized to accommodate all or part of a thumb for easy carrying. In one embodiment, the depth of the thumb depressions 16a and 16b is about half the thickness of the tray 10. Obviously, other grasping features, such as handles, can be incorporated in the tray of the present invention instead.

The tray 10 may further include a support, which can make it easier to lift the tray from a level surface such as the top of a table, a cart or a counter. The support can have one or more legs. In the particular embodiment shown in FIG. 1, three foldable legs are attached to the bottom surface or the perimetrical surface 14. Two of them, 18a and 18b are visible in FIG. 1 and are each attached to the bottom surface through a hinge 20a and 20b.

An array of depressions are disposed on the top surface 12 of the tray 10 for receiving and holding multiple objects useful in nursing. The number and types of the depressions may vary without departing from the spirit of the invention. Depth of the depressions may vary, e.g., about half the thickness of the tray, as long as they can hold the intended object securely. They are preferably organized in easily recognizable patterns so that the user can quickly find the right depression to put a given object. In the illustrated embodiment, a row (or, optionally, multiple rows) of substantially round depressions is centrally located, i.e., substantially in the middle section of the tray, for receiving small receptacles, preferably of substantially round cross-sections. This helps to stabilize the entire tray as the expected round receptacles can be the heaviest objects on the tray as they often carry various kinds of liquid. Preferably, the row(s) of round depressions is also roughly aligned with a "grasping line" 25 (best viewed in FIG. 2) between the two thumb depressions (16a and 16b). This is particularly advantageous for carrying open receptacles which helps the user balance the tray during the transport without spilling the content of any open receptacles. Three of such round depressions are shown as 22, 24 and 26. The central depression 22 is the largest for carrying the largest receptacle, presumably with the largest amount of liquid. In this embodiment, the central depression 22 is located in the center of the round, top surface of the tray 10. The other two depressions 24 and 26 may be of substantially the same size so that the receptacles they carry tend to balance out in weight. Again, if the weight of the receptacles and their contents in depressions 24 and 26 are not the same, it is much easier for the user to balance the tray during transport as the two depressions line up with the two thumb depressions (16a and 16b).

Space for multiple receptacles is envisioned as a patient often requires more than one medication, solid or liquid, and sometimes they need to be taken with more than one liquid, e.g., water, juice and syrup. Some of the intended receptacles include pill bottles or containers, soufflé portion cups, paper cups, plastic cups, liquid bottles, lotion or gel bottles or tubes, and cups of any material. In one embodiment, depressions 22-26 are sized to fit receptacles that are designed to carry liquids of an amount between 0.5 and 10 ounces. For example, if the envisioned receptacles are calibrated plastic medication cups with respective capacity for 0.5, 0.75, 1.0, 1.25, 1.5, 2.0, 3.0, 3.5, 4.0, 5.0 and 9.0 oz of fluid, the diameters of the depressions 22-26 may vary from about 1.0 inches to about 3.0 inches, preferably in the range of 1.0 to 2.0 inches. The depressions 22-26 may be substantially cylindrical, i.e., the diameters of the opening and the bottom of the depression are substantially the same. Or, the depressions 22-26 may be part of a conical structure, i.e., there is a taper in the side-wall such that the diameters of the opening and the bottom of the depression are not the same. Typically, the bottom would be smaller than the opening to correspond to the shape of a typical liquid receptacle. Obviously, the number of substantially round depressions may be other than three in an embodiment.

In one particular embodiment, the central depression 22 has an opening that measures about 2.0 inches in diameter, while both depressions 24 and 26 have an opening that measures about 1.0 inch in diameter.

Still referring to the illustrative embodiment shown in FIGS. 1 and 2, on one side of the central row of round depressions is an elongated depression or slot 28, which can be used for receiving a number of objects, such as a syringe, a notepad (e.g., Post-it® notes), a straw, a spoon, a tongue depressor, or a writing instrument. Depending on the intended use, there may be one or more of such slots shaped and sized to fit the objects in mind. In a preferred embodiment, the slot's long axis runs substantially parallel to the "grasping line" 25 (FIG. 2) defined by the two thumb depressions (16*a* and 16*b*) for balance purposes.

In the illustrated embodiment, there is also a substantially oval depression 30. It may be located anywhere on the top surface 12 of the tray of course, but where it is a relatively small depression, it may be located closer to the periphery than the center of the round tray 10 as illustrated here. FIGS. 3A-3D illustrate some examples of "substantially oval" shapes. Depressions of such shapes have proved to be useful because many receptacles used in healthcare have cross-sections of these shapes. Examples of such receptacles include those for nasal sprays.

Referring back to FIG. 1, on the other side of the central row of round depressions is a substantially planar display 32 situated at an angle for displaying information, such as patient identity and medication information. Patient identity information can include the last name, first name, room number and bed number (i.e., location information). The display 32 can include a writable surface for directly writing upon it, or configured to hold a pre-marked (e.g., computer printed) strip. At the back of the display 32 is a structure that holds a writing instrument. In the illustrated embodiment, two loops 34*a* and 34*b* between the display 32 and the top surface 12 serve this purse as one can fasten the cap of a pen onto the loop or slide the body of the pen through at least one of the loops.

Referring now to FIG. 2, which is a top view of the tray 10. In particular, according to one feature of this embodiment, the long axes of each row or depression and of the display are all aligned and substantially parallel to the "grasping line" 25 between the two thumb depressions (16*a* and 16*b*) for better balance and ease of handling. In one feature, a symmetric arrangement is provided for further advantage in stability. An orthogonal line 34 runs perpendicular through the midpoint 27 of the grasping line 25, dividing the tray 10 into two substantially even halves. In an optional feature, all depressions and the display 32 may be situated symmetrical about this orthogonal line 34.

Referring now to FIG. 4, another embodiment 40 of the invention is illustrated through a top view. The tray 40 is substantially rectangular with multiple depressions and a display 42, optionally with the pen-holding loops in the back, all similar to the ones described above. There are two rows of depressions in a relatively central section of the tray. One row 44 consists of substantially round depressions 46*a*-46*d*. In this particular case, the four depressions 46*a*-46*d* are of substantially the same size. The second row 47 has two substantially round depressions 48 and 50, and a substantially oval depression 52. These depressions are similar to those described with regard to tray 10. In one embodiment, each of the depressions 46*a*-46*d* is shaped and sized to accommodate a 1.25 oz soufflé cup, and depressions 48 and 50 are shaped and sized to accommodate a 5 oz and a 10 oz soufflé cup, respectively.

An elongated slot 54 sized and shaped for receiving a straw is also provided. Two substantially rectangular slots 56 and 58 are also provided. They can receive and accommodate a notepad (e.g., Post-it® notes), instruction sheets, wipes, toiletries, waste, and so on. A depression 60 sized and shaped for receiving a syringe is provided. It has a narrow tip 62 to orient the placement of the syringe. A distal notch 64 is provided to accommodate the rim of the needle cap. And a middle notch 66 is provided to accommodate both the proximal end of the syringe and the handle of the plunger in a collapsed state of the syringe, i.e., when the plunger is pushed against the proximal end of the syringe barrel. A proximal notch 68 is provided to accommodate the handle of the plunger in the extended state, i.e., when the plunger is pulled all the way away from the barrel. In one embodiment, the syringe slot 60 is about 7 inches long and can accommodate syringes of 20-50 cc capacity. Finally, a depression 70 sized and shaped for receiving a spoon is specifically provided.

The tray 40 is preferably dimensioned to fit a drawer of a medication cart. In one embodiment, it is about 12 inches by 9 inches. It may optionally have grasping features such as the thumb depressions described above and support features such as the foldable legs described above.

It is hereby noted that by "to receive" or "to accommodate," it does not necessarily mean to fit the entire object. With receptacles, it is sufficient to fit a bottom portion of the receptacles. And with elongated objects, fitting part of the body is sufficient in most cases. Therefore, for example, the slot 54 in the second illustrated embodiment does not have to be longer than a straw-in fact, slight shorter may be more advantageous as one end of the straw will stick out and be ready to be picked up.

Trays of the present invention may be made of any suitable material by a suitable process well known to one skilled in the art. Such materials include plastics and metals, and, preferably, can be sanitized.

While the present invention has been particularly shown and described with reference to the structures and methods disclosed herein and as illustrated in the drawings, it is not confined to the details set forth and this invention is intended to cover any modifications and changes as may come within the scope and spirit of the following claims.

I claim:

1. A tray for transporting and serving medication, the tray comprising:
    a planar circular body with a center point, the body having a circular top surface and a circular bottom surface, the body further having a perimetrical surface connecting at least part of the top surface and part of the bottom surface and defining a general thickness of the tray;
    a first grasping feature on a first side of the body;
    a second grasping feature on a second side, the second grasping feature being disposed opposite the first grasping feature on the circular body, wherein the first and second grasping features together define a first balancing line across the top surface that bisects the top surface into two halves of equal area;
    a second balancing line that passes through the center point of the circular body and intersects the first balancing line at a right angle to provide an intersection at the center point of the circular body; and
    at least three circular depressions situated on the top surface and in the first balancing line forming a row, at least two of the depressions having different diameters, the three circular depressions including a central depression situated at the center point of the circular body, each depression sized and shaped for receiving a receptacle.

2. The tray of claim 1 wherein the row has a middle and the central depression is larger than the other depressions, such depression being situated in the middle of the row for receiving the largest receptacle.

3. The tray of claim 1 further comprising at least one elongated depression, wherein its long axis runs parallel to the first balancing line and perpendicular to the second balancing line.

4. The tray of claim 1 further comprising a second row of depressions, the second row having a long axis that runs parallel to the first balancing line.

5. The tray of claim 1, further comprising a display situated on the top surface at an angle for displaying information.

6. The tray of claim 5, further comprising a loop between the display and the top surface of the tray for fastening a writing instrument thereonto.

7. The tray of claim 1 wherein each of the plurality of depressions is sized and shaped for receiving a receptacle with a round cross-section.

8. The tray of claim 1, further comprising an elongated depression sized and shaped for receiving a syringe.

9. The tray of claim 8, wherein the elongated depression has a longitudinal axis, the elongated depression comprises two notches, spaced from one another along the longitudinal axis, for receiving the syringe in either an extended or a collapsed state.

10. The tray of claim 1, further comprising an oval depression sized and shaped for receiving a receptacle with a oval cross-section.

11. The tray of claim 1, wherein at least one of the grasping features comprises a depression situated along an outer edge of the top surface sized and shaped to accommodate at least part of a thumb.

12. The tray of claim 1 further comprising at least two legs for supporting the tray.

13. The tray of claim 12 wherein the legs are foldable.

14. The tray of claim 1 wherein the tray is sized to fit into a drawer of a medication cart.

15. The tray of claim 1 wherein the tray is less than about 16 inches in length and less than about 10 inches in width.

16. A tray for transporting and serving medication, the tray comprising:
 a planar circular body with a center point, the body having a top surface and a bottom surface, the body further having a perimetrical surface connecting at least part of the top surface and part of the bottom surface and defining a general thickness of the tray;
 a first thumb depression on a first side of the body sized and shaped to accommodate at least part of a thumb;
 a second thumb depression on a second side of the body, the second thumb depression being disposed opposite the first thumb depression on the circular body, the second thumb depression also sized and shaped to accommodate at least part of a thumb, wherein the first and second thumb depressions together define a first balancing line across the top surface that bisects the top surface into two halves of equal area, the first balancing line passing through the center point;
 a second balancing line that passes through the center point of the circular body and intersects the first balancing line at a right angle to provide an intersection at the center point of the circular body;
 a row of at least three circular depressions situated on the top surface and in the first balancing line, at least two of the depressions having different diameters, each depression sized and shaped for receiving a receptacle, wherein the largest among the plurality of depressions is a central depression situated in the middle of the row and at the center point of the circular body for receiving the largest receptacle;
 an elongated depression;
 a oval depression sized and shaped for receiving a small receptacle with a oval cross-section; and
 a planar display situated on the top surface at an angle for displaying information, wherein the second balancing line runs through a midpoint of the first balancing line thereby dividing the body into two even halves, and all the depressions and the display are situated symmetrically about the second balancing line.

17. The tray of claim 16, wherein the elongated depression has a longitudinal axis, the elongated depression comprises two notches, spaced from one another along the longitudinal axis, sized and shaped for receiving a syringe in either an extended or a collapsed state.

18. The tray of claim 16, further comprising a second elongated depression sized and shaped for receiving a straw, a third elongated depression sized and shaped for receiving a spoon, and a rectangular depression sized for receiving a note pad.

19. A tray for transporting and serving medication, the tray comprising:
 a planar circular body with a center point, the body having a top surface and a bottom surface, the body further having a perimetrical surface connecting at least part of the top surface and part of the bottom surface;
 a first depression on a first side of the body sized and shaped to accommodate at least part of a thumb;
 a second depression on a second side of the body, being disposed opposite the first depression on the circular body, the second depression also sized and shaped to accommodate at least part of a thumb, wherein the first and second depressions together define a first balancing line across the top surface that bisects the top surface into two halves of equal area, the first balancing line passing through the center point;
 a second balancing line that passes through the center point of the circular body and intersects the first balancing line at a right angle to provide an intersection at the center point of the circular body, the tray and all depressions thereon being symmetrical about the second balancing line;
 a first row of at least three circular depressions situated on the top surface and in the first balancing line, at least two of the depressions having different diameters, each depression sized and shaped for receiving a receptacle, wherein the largest among the plurality of depressions is a central depression is situated in the middle of the row and at the center point of the circular body for receiving the largest receptacle;
 an elongated depression whose longitudinal axis runs parallel the first balancing line and the elongated depression being symmetrical about the second balancing line;
 at least one oval depression; and
 a planar display situated on the top surface at an angle for displaying information;
 wherein the second balancing line runs through a midpoint of the first balancing line thereby dividing the body into two even halves, and all the depressions and the display are situated symmetrically about the second balancing line.

* * * * *